(12) United States Patent
Rahman (10) Patent No.: US 6,729,877 B2
(45) Date of Patent: May 4, 2004

(54) DENTAL INSTRUMENT HAVING ENLARGED HANDLE AND GLUED CONE

(75) Inventor: Anisur Mithu Rahman, Gurnee, IL (US)

(73) Assignee: Hu-Friedy Mfg. Co., Inc., Chicago, IL (US)

( * ) Notice: Subject to any disclaimer, the term of this patent is extended or adjusted under 35 U.S.C. 154(b) by 123 days.

(21) Appl. No.: 10/039,359

(22) Filed: Nov. 7, 2001

(65) Prior Publication Data

US 2003/0022130 A1 Jan. 30, 2003

Related U.S. Application Data (60) Provisional application No. 60/308,624, filed on Jul. 30, 2001.

(51) Int. Cl.[7] .............................................. A61C 3/00
(52) U.S. Cl. ........................................................ 433/141
(58) Field of Search ............................... 433/141, 142, 433/143, 146, 147; 16/421, 430; 81/489, 491, 492; 172/371

(56) References Cited

U.S. PATENT DOCUMENTS

| | | | |
|---|---|---|---|
| 2,818,647 A | | 1/1958 | Berliner |
| 3,090,653 A | * | 5/1963 | Stump .......................... 403/248 |
| 3,602,277 A | * | 8/1971 | Stump ............................. 81/20 |
| 4,060,897 A | | 12/1977 | Greenstein |
| D249,062 S | | 8/1978 | Crafoord et al. |
| 4,352,381 A | * | 10/1982 | Provi ......................... 30/308.1 |
| 4,759,713 A | | 7/1988 | Heiss et al. |
| 4,795,344 A | | 1/1989 | Brewer, Jr. |
| 4,841,597 A | * | 6/1989 | Kolonia ........................ 16/422 |
| 4,882,867 A | | 11/1989 | Linden |
| 4,988,295 A | | 1/1991 | Kline |
| 5,031,272 A | * | 7/1991 | Carmien ..................... 16/110.1 |
| 5,090,907 A | | 2/1992 | Hewitt et al. |
| 5,100,321 A | | 3/1992 | Coss et al. |
| 5,477,929 A | * | 12/1995 | Kenyon et al. .............. 172/372 |
| 5,498,158 A | | 3/1996 | Wong |
| 5,501,597 A | | 3/1996 | Wilson |

(List continued on next page.)

FOREIGN PATENT DOCUMENTS

DE         3722368 A1     1/1989

OTHER PUBLICATIONS

American Eagle Instruments, Inc., We've Got "The Handle" on Carpal Tunnel, Published before Jul. 31, 1996.
Hu–Friedy Dutch Catalog, Published before Jul. 31, 1996.
European Search Report for European Application 02255269.9–1265, counterpart of above–identified application, dated Mar. 28, 2003 with Annex (3–page document).

Primary Examiner—Todd E. Manahan
(74) Attorney, Agent, or Firm—Welsh & Katz, Ltd.

(57) ABSTRACT

A dental instrument has an elongated handle, in one embodiment, a molded resin handle which incorporates an elongated metal insert, and in another embodiment, a metal handle. At least one tip carrying cone is slidably received into a hollow end of the respective handle after adhesive has been injected into the respective end of the handle. As the stem of the cone slides into the handle and through the adhesive, the adhesive flows into the stem and around and through torque lock features in the stem. Features include one or more slots in the stem or alternately one or more holes or protrusions in or on the stem. When the adhesive cures a solid mass of adhesive engages the torque lock feature and in combination with the interior periphery in the handle, the instrument exhibits an ability to pass applied torque tests on the order of 400 newton-centimeters without damage or relative motion between the operative tip and the resin handle.

29 Claims, 7 Drawing Sheets

U.S. PATENT DOCUMENTS

| | | |
|---|---|---|
| 5,578,050 A | 11/1996 | Webb |
| D394,902 S | 6/1998 | Herbst et al. |
| 5,816,806 A | 10/1998 | Herbst et al. |
| 5,842,861 A | 12/1998 | Buchanan |
| 5,893,713 A | 4/1999 | Garman et al. |
| 5,934,905 A | 8/1999 | Martoral et al. |
| 6,042,378 A | 3/2000 | Fischer et al. |
| 6,109,918 A | 8/2000 | Hammond et al. |
| 6,190,168 B1 * | 2/2001 | Bowen ....................... 433/127 |
| 6,261,099 B1 | 7/2001 | Senia et al. |
| 6,427,563 B1 * | 8/2002 | Zurbuchen et al. ........ 81/177.1 |

* cited by examiner

DENTAL INSTRUMENT HAVING ENLARGED HANDLE AND GLUED CONE

This application claims the benefit of the earlier filing date of Provisional Application Ser. No. 60/308,624 filed Jul. 30, 2001.

FIELD OF THE INVENTION

The invention pertains to dental instruments. More particularly, the invention pertains to such instruments with large diameter, more comfortable handles.

BACKGROUND OF THE INVENTION

A number of dental instruments, such as scalers, have been marketed with elongated plastic handles as an alternate to traditional metal handles. Light weight, relatively large diameter resin handles are preferred by some dental professionals as they tend to reduce hand fatigue. Larger diameter resin handles not only are comfortable to use, but their weight does not increase significantly due to lower density of the resin when compared to stainless steel, aluminum or brass.

Resin handles have advantages in that they usually exhibit lower manufacturing cost than is the case with stainless steel, aluminum, brass or ceramic handles. In addition, resin permits greater design latitude than is the case with metal.

Known resin handled scalers have a diameter on the order of 0.375–0.410 inches. Metal scalers have handles with diameters on the order of 0.270–0.375 inches.

Known resin handle scalers have however certain limitations. Many known resin handled instruments do not appear capable of passing the currently specified torque test of ISO 13397-1 issued Dec. 15, 1995. That test mandates that an applicable instrument must be able to pass an applied torque test of 35.4 inch-pounds (400 newton-centimeters) without damage or relative motion between the instrument's operating tip and the respective resin handle. Some commercially available scalers with resin handles can tolerate only about 18 inch-pounds of applied torque without damage or relative motion between handle and tip.

One way to increase the amount of torque which the instrument can resist is to increase the force necessary to press fit the tip of the instrument into the handle. This technique, which increases the interference between mating surfaces, is not suitable for use in resin handled instruments.

A greater degree of torque resistance can be attained by using a tubular metal insert around which the resin handle is molded. The tip can then be press fit into the metal insert. However, the thin wall of the insert may deform outwardly to some extent in this process creating undesirable circumferential hoop stress in the ends of the resin handle. This hoop stress can shorten the life of the instrument and is to be avoided.

Increasing the thickness of the wall of the insert tends to reduce hoop stress at the expense of adding weight to the instrument. The increased weight detracts from the advantages of using resin making this a less desirable solution.

There continues to be a need for light-weight resin handles which can pass the ISO 13397-1 torque test. Preferably such instruments would have usable lives comparable to traditional metal instruments.

SUMMARY OF THE INVENTION

The present instrument is, in one embodiment, formed of an injection molded handle with a metal insert preferably hollow, through its center to provide structural reinforcement. A tapered metal cone is attached at at least one end to smoothly transition the molded handle to a smaller instrument tip. The cone may or may not have a finger pad or a band, which fits snugly in a groove located on the cone. The cone is preferably attached to the handle with adhesive.

The metal insert is placed inside a mold. Resin is then injected around the insert. The resin fills the mold to the desired shape and forms the desired handle geometry. The centrally located metal insert becomes an integral part of the structure.

To be sure that this insert will not separate from the resin, at least one spiral groove is formed on the outer surface of the insert. Preferably, two separate spirals are cut on the insert's surface, one from each end. The opposing spirals neutralize the occurrence of any potential thermally induced axial forces.

Since the handle is repeatedly sterilized, it is conceivable that over time the insert could start to shift inside the resin in one direction. This may create an undesirable configuration as the cone will begin to separate from the main body. A double spiral configuration minimizes the likelihood of development of such unidirectional forces.

The spiral design also serves to achieve both axial and torsional interlock. Since the resin gets trapped inbetween the spiral features, the insert can neither rotate nor translate. This provides for a secure bond between the insert and the exterior handle.

A tip receiving cone for a dental instrument has a body with a hollow stem with a free end and a displaced tip receiving region. An adhesive, or glue, engaging feature is carried adjacent to the free end.

In one embodiment, the feature is an opening for example a slot or hole, formed in the stem. In another embodiment, the feature is a protrusion on the stem. The feature, combined with adjacent cured adhesive, resists larger amounts of applied torque than is achievable using only the shear strength of the adhesive.

Where the feature is a slot or hole in the stem, the cured adhesive in the slot or hole forms a physical barrier to rotation of the stem. A similar result can be obtained with a surface or member that protrudes from the stem.

The cone can be used with a relatively large diameter plastic handle that has a central hollow metal insert. The plastic handle could have an exemplary diameter on the order of 0.390 inches. The insert could have an exemplary diameter on the order of 0.219 inches.

The end or ends of the insert can be filled with adhesive. The cone can be inserted into the insert, in part with an interference fit.

The adhesive fills the stem and the areas abutting the feature, slot or protrusion. When cured, in the case of the slot, a barrier of adhesive extends through the slot blocking rotation of the cone relative to the handle.

The solid adhesive barrier in combination with the cone and metal insert resist applied torque in excess of 30 inch-pounds with a relatively light-weight metal insert. This result can be achieved with reduced interference, less of a press-fit, between the hollow end of the insert and the stem of the cone and without subjecting the plastic handle to undesirable hoop stress.

The metal cone is attached to the handle by pressing it into an open end of the metal insert inside the handle. The inside diameter of the insert is controlled at one or both ends to provide a selected press fit.

A bead of epoxy glue is used to hold the cone securely in pace once the glue has been cured. The epoxy glue is repeatedly sterilizable.

A slot, or hole, is formed at the end of the stem of the cone. As the cone is pressed in place, the glue flows into the cutout. The glue remains trapped in that location even after curing. In addition to the shear strength of the glue, the cured, hard mass of trapped glue provides a mechanical inter-lock, which significantly increases the torsional strength of the instrument.

The additional torsional strength is achieved without increasing the force needed to press fit the cone into the insert. Hoop stress, which is particularly detrimental in resin handles, can increase exponentially with an increase in press fit forces. A build up of such hoop stress at each end, although invisible when the instrument is new, can lead to premature failure of the resin when subjected to repeated sterilization. The slot or hole at the free end of the cone, helps to achieve the desired torsional strength, on the order of 400 newton-centimeters, without increasing the press-fit (the hoop stress causing mechanism) thereby maintaining the structural integrity of the instrument.

The same concept may be applied also to metal handles. In metal handles the cone is often brazed to the handle since the metals can survive the brazing temperatures. The necessary torsional strength is achieved from the brazed joint. However, this process is fairly expensive.

An alternate process would be to use epoxy glue instead of the braze paste. Providing the slot at the handle-end of the cone increases torsional strength of the instrument.

Alternate glue engaging features can be used instead of the above noted slot. For example, one or more holes can be cut into the stem of the cone. As the cone is pressed into place, the adhesive or glue flows into the hollow stem and into and through the hole or holes. When cured, the adhesive, extending through the hole or holes, blockingly engages the cone thereby preventing rotation.

Alternately, a flange or shoulder can extend radially from the stem. When inserted, the flange or shoulder protrudes into and abuts the adhesive. When cured, glue, or adhesive, located adjacent to the flange locks rotation of the cone relative to the insert.

In one aspect, the metal cone is attached to the handle by press fitting it into a glue filled metal tube that is centered in a molded resin handle. The inside diameter of this tube is controlled at each end to provide a press fit without imparting excess hoop stress to the end of resin handle.

As the cone is pressed in place in the tube, the glue flows into the cone and flows around a glue engaging feature. The glue remains trapped in that location after curing.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENTS

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

Figure 1:
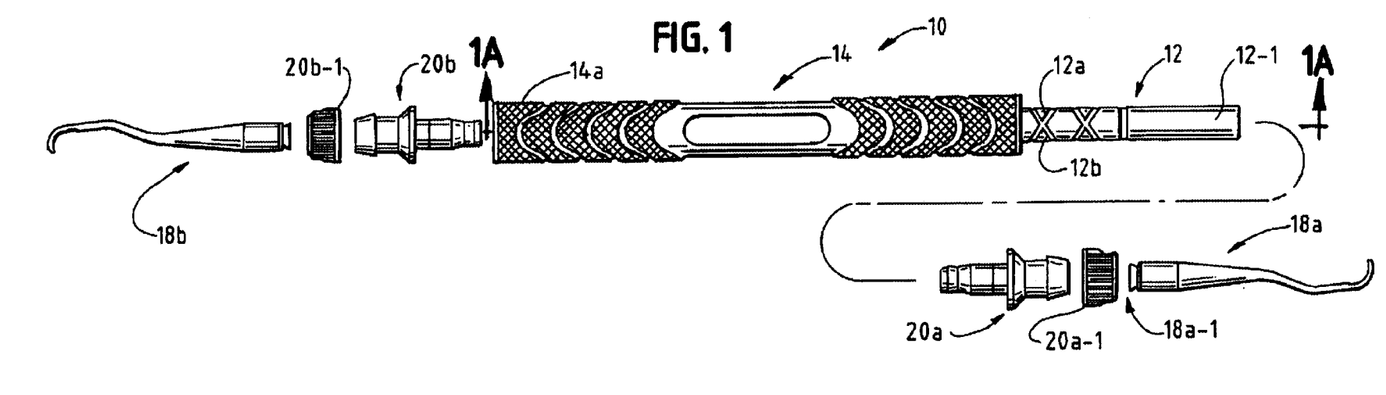
FIG. 1 is an exploded view of an exemplary instrument in accordance with the present invention.

FIG. 1 illustrates an instrument 10 in accordance with the present invention. The instrument 10 includes a reinforcing hollow core or insert 12 which has formed thereon, by cutting or any other form of processing, dual reverse spirals 12a and 12b.

An elongated resin handle generally indicated at 14 is molded around the reinforcing insert 12. The resin 14a flows into the dual spirals 12a, 12b and when cured is locked to the insert 12 thereby precluding axial and/or rotary movement between insert 12 and handle 14.

The dual spirals 12a, 12b formed in the insert 12, to which the handle 14 is bonded, overcome potential, thermally induced, axial forces such that the insert 12 cannot move axially due to expansion produced from sterilization heat. Additionally, the bonding between the resin handle 14 and the spirals 12a, 12b in the insert 12 locks the handle 14 and insert 12 together so as to block both axial and rotary movement therebetween when in use.

It will be understood that a variety of instruments can be used to cut or form the dual reverse spirals 12a, 12b in the exterior periphery of the insert 12. Additionally, the cross section of the spirals 12a, 12b may vary without departing from the spirit and scope of the present invention. Representative cross sections include generally rectangular, triangular, partly or semi-circular, or elliptical. The bottom edges of the spirals can be formed slightly rounded to minimize stress concentration in the insert 12.

Figure 1A:
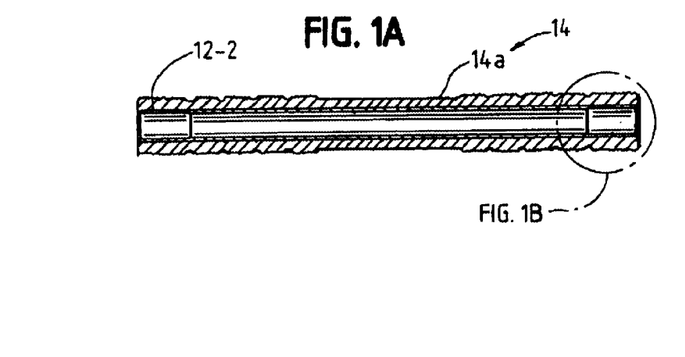
FIG. 1A is a sectional view, illustrating details of the handle of FIG. 1, taken along plane 1A—1A of FIG. 1.
Figure 1B:
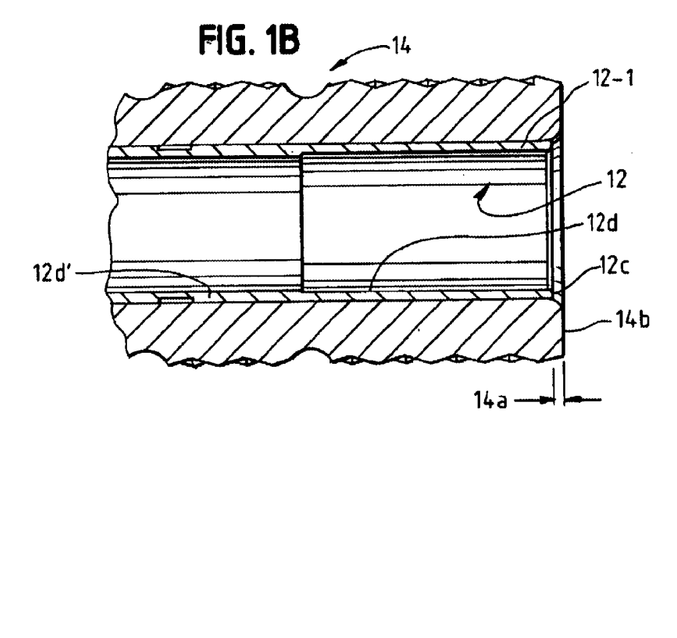
FIG. 1B is an enlarged sectional view of a portion of an end of the handle of FIG. 1A.
Figure 1C:
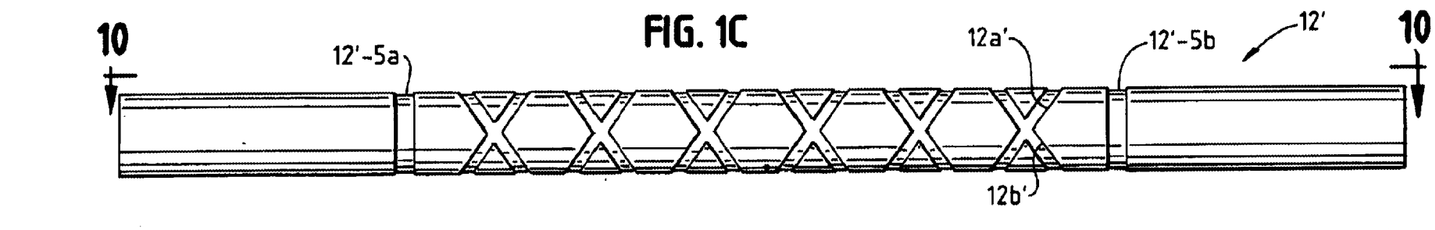
FIG. 1C is an enlarged side elevational view of an alternate insert usable in the instrument of FIG. 1.
Figure 1D:
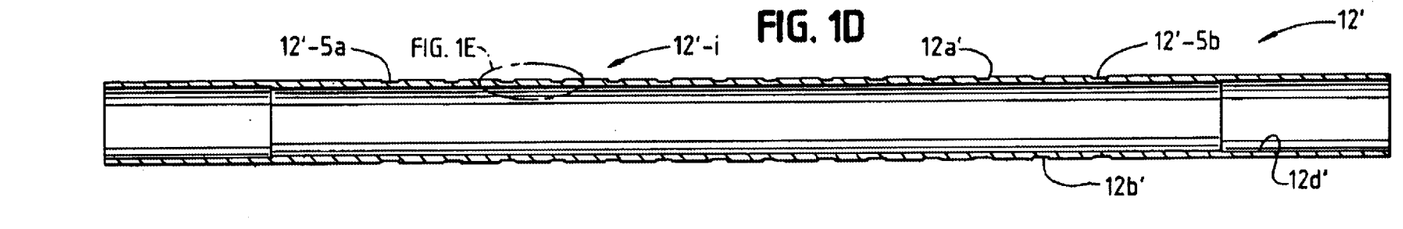
FIG. 1D is an enlarged sectional view taken along plane 1D—1D of FIG. 1C.
Figure 1E:
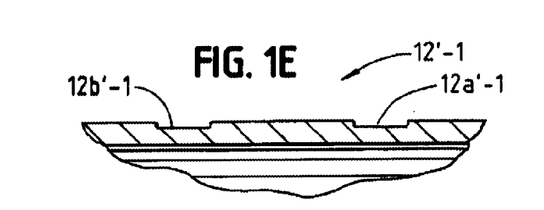
FIGS. 1E–1H are fragmentary enlarged views of a portion of the insert of FIG. 1D.
Figure 1F:
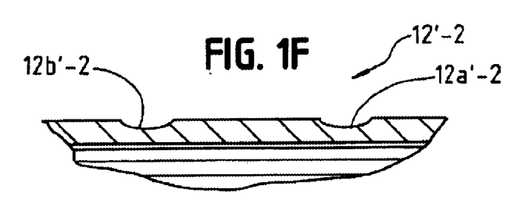
Figure 1G:
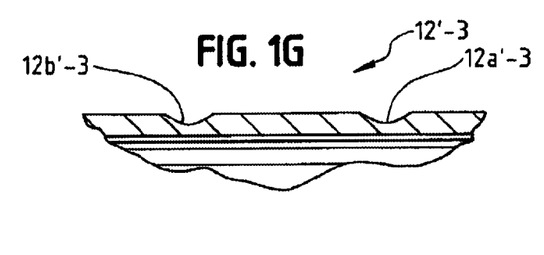
Figure 1H:
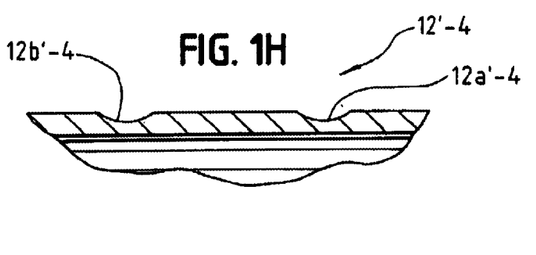

As an alternate to insert 12, FIGS. 1C, 1D illustrate an insert 12' which has dual reverse spirals 12a', b'. The various exemplary cross-sections of spirals 12a', b' from region 12'-i are illustrated in FIGS. 1E–1H. Other cross sections are possible and come within the spirit and scope of the present invention.

Rings 12'-5a, b can be formed in insert 12' and provide additional features which resin 14a can engage with and lock onto when cured.

FIG. 1A illustrates insert 12 bonded to handle 14 in section. As best illustrated in FIG. 1B, the design of the handle includes an overhang 14a, illustrated at each end of handle 14 relative to insert 12. The presence of the overhang 14a at each end of the handle 14 compensates for a potentially higher degree of axial expansion of the insert 12, compared to resin handle 14, during sterilization so that end 12c of insert 12 never extends beyond end 14b of resin handle 14. It will be understood that a single ended instrument will exhibit the same configuration at the end where the instrument or mirror is attached.

It will be understood that resin handle 14 can be molded of any suitable medical grade plastic, or elastomers including silicon, without departing from the spirit and scope of the present invention. Further, while preferably the overhang 14a is on the order of fifteen thousandths of an inch, between the end 12c of the insert 12 and the end 14b of the resin handle, it will be understood that other amounts of overhang come within the spirit and scope of the present invention.

Instrument 10 is illustrated for purposes of the present disclosure as a double ended instrument having treatment applying tips 18a, 18b. The shape of the tips 18a, 18b can vary, depending on the desired type of instrument, without departing from the spirit and scope of the present invention. It will also be understood that single ended instruments having only a single operative tip, such as tip 18a, or perhaps a mirror, come within the spirit and scope of the present invention.

Each of the tips 18a, 18b is coupled to a respective end of handle 14 by means of a respective cone 20a, 20b. Each of the cones 20a, 20b is substantially identical so a discussion of cone 20a will also describe cone 20b.

Figure 2:
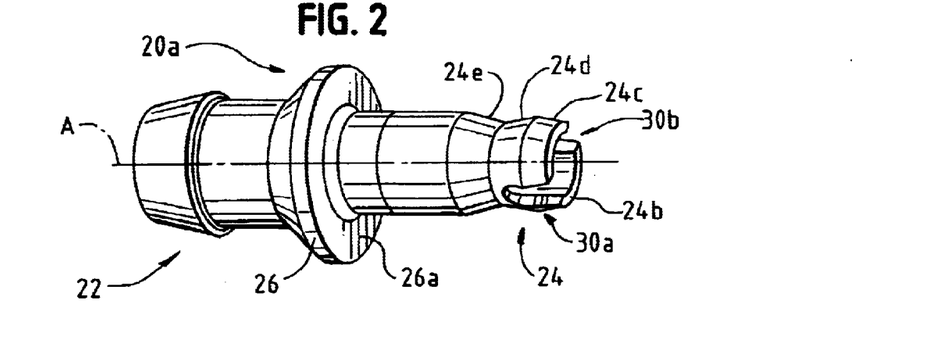
FIG. 2 is a perspective view of an instrument carrying cone of a type usable in the instrument of FIG. 1.
Figure 3:
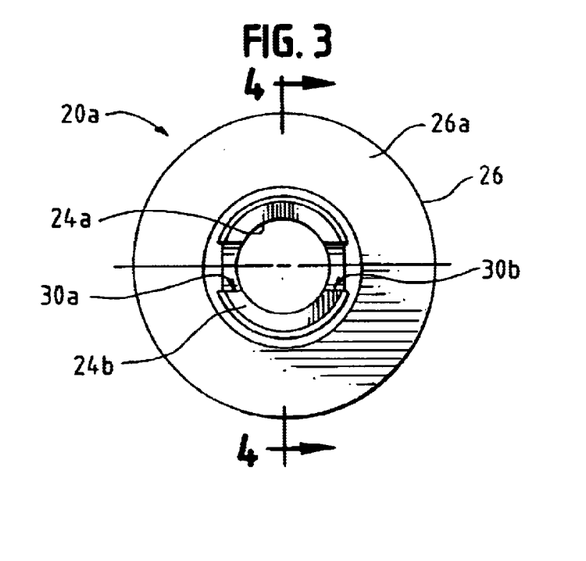
FIG. 3 is an end view of the cone of FIG. 2.
Figure 4:
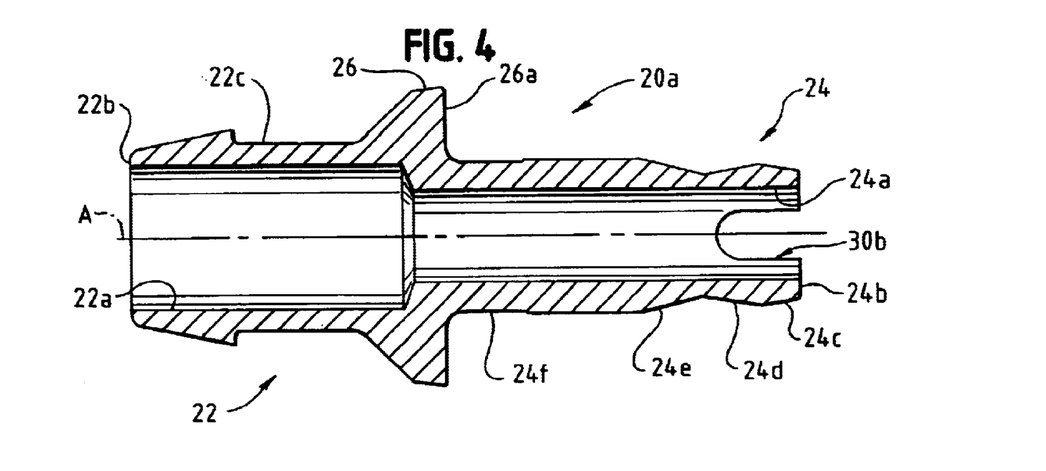
FIG. 4 is a side sectional view of the cone of FIG. 3 taken along plane 4—4 of FIG. 3.

As illustrated in FIGS. 2–4, cone 20a has a first, or instrument, receiving end generally indicated at 22 and a second or stem end 24. Instrument receiving end 22 is hollow with an interior peripheral surface 22a which terminates at an exterior end 22b. During the assembly process, a proximal end 18a-1 of the tip 18a is press-fit into the instrument receiving end 22.

A cylindrical surface 22c slidably receives an elastomeric color coded overlay, such as overlays 20a-1, 20b-1. In addition to color coding, to identify type of instrument, office or procedure, overlays 20a-1, 20b-1 provide additional non-slip surfaces for a practitioner's fingers while using the instrument 10.

The stem 24 is formed with a cylindrical interior peripheral surface 24a which extends axially along a central axis "A" of the cone 22. Stem 24 also exhibits, on an exterior peripheral surface thereof, first and second oppositely tapered, abutting, surfaces 24d, e which intersect and form, as discussed in more detail below, an adhesive or glue trap with an interior peripheral surface 12d of the insert 12.

Tapered surface 24e terminates at a cylindrical exterior peripheral region 24f of stem 24 which in turn abuts an enlarged annular region 26. The region 26 is interposed between the insert receiving region 22 and the stem 24. When assembled, an annular surface 26a abuts end 14b of resin handle 14.

A pair of slots 30a, 30b is formed in the stem 24 adjacent to end 24b. The slots 30a, 30b can be formed in a variety of shapes without departing from the spirit and scope of the present invention.

When instrument 10 has been assembled, as discussed in more detail subsequently, the slots 30a, 30b provide a torque lock which couples insert 12 to cone 20a thereby precluding rotation therebetween in response to applied torques of at least 400 newton-centimeters in accordance with ISO 13397-1.

Figure 5:
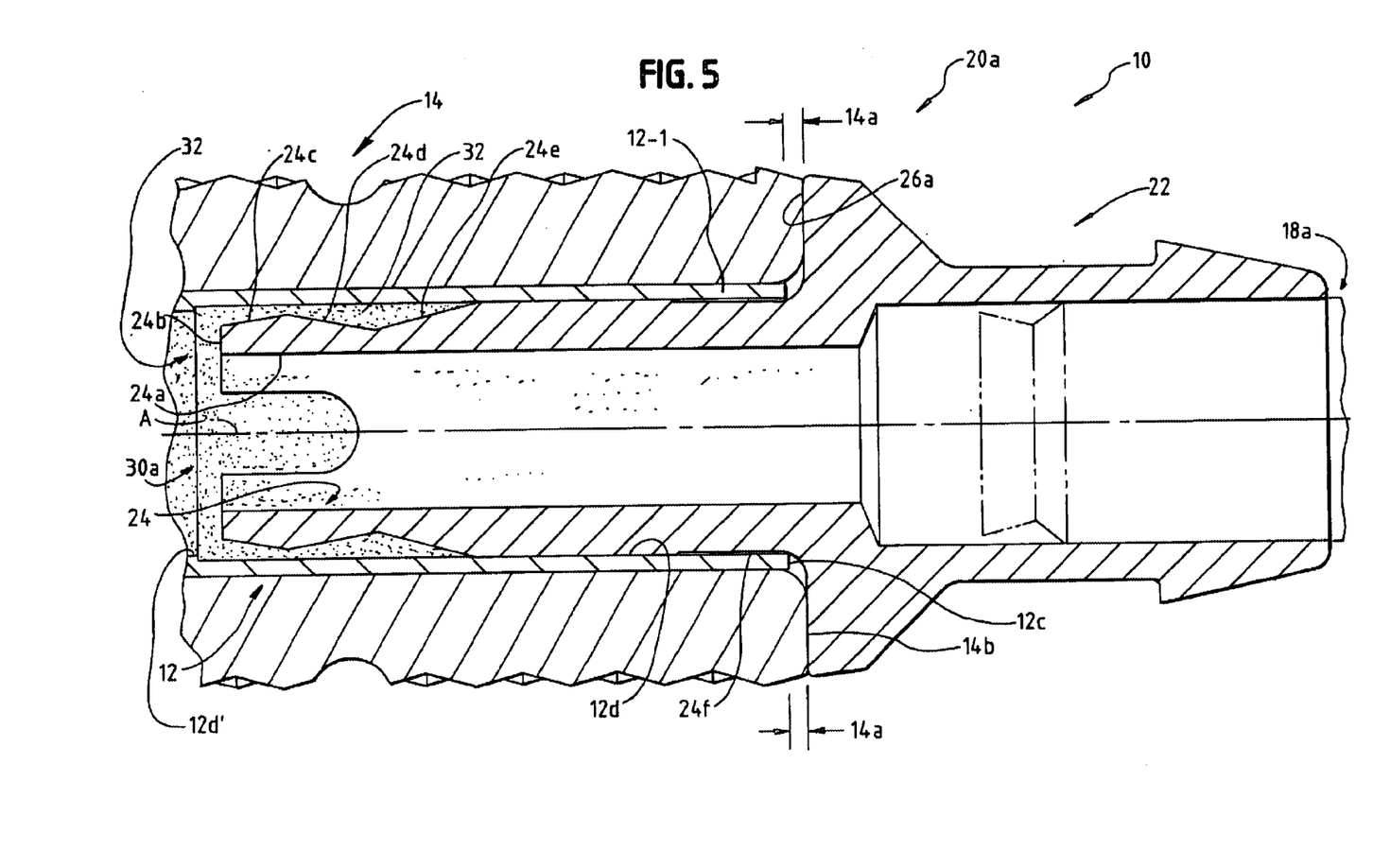
FIG. 5 is an enlarged sectional, fragmentary view of an end of the instrument of FIG. 1 illustrating further details of the relationship between the components thereof.

FIG. 5 illustrates in more detail the relationship between insert 12, handle 14 and representative cone 20a when assembled together. As illustrated in FIG. 5, stem 24 is slidably received into a hollow end of insert 12, perhaps with a press-fit, in the vicinity of peripheral surface 24f if desired.

Prior to inserting cone 20a, the end of the insert 12 has been filled with a glue or adhesive 32, such as an epoxy. As the stem 24 slides along the internal peripheral surface 12d of insert 12, the adhesive 32 fills the glue trap formed of abutting, reverse tapered surfaces 24d, 24e as well as the slot or slots 30a, 30b. In the process, the glue 32 also flows into the hollow interior of stem 24 bounded by surface 24a.

When the adhesive 32 has cured, a solid mass fills the annular glue trap formed by reverse tapered surfaces 24d, 24e and interior cylindrical surface 12d. This mass extends between slots 30a, b into hollow stem 24 generally in contact with interior peripheral surface 12d.

The cured adhesive 32 is effective not only to block axial movement of cone 20a during use but also blocks rotary movement of cone 20a relative to stem 12 in response to applied torque during use. The locking structure of the cured adhesive in the slots 30a, 30b as well as in contact with the internal peripheral surface 12d of insert 12 is highly effective in resisting rotation of the cone 20a due to applied torque.

It will be understood that the exact details of assembly of the instrument 10 are not a limitation of the present invention. In this regard, the operative tips, such as tip 18a, can be press-fit into the respective cone, such as cone 20a, either before or after the cones 20a, 20b is/are glued into the respective insert 12 and handle 14.

FIG. 5 also illustrates overhang 14a between end 12c of insert 12 and end 14b of handle 4. Surface 26a abuts the end 14b of the handle 14.

While cone 20a has been preferably described as having slots 30a, 30b, it will be understood that other numbers and shapes of slots such as 1, 3, or more come within the spirit and scope of the present invention. Instead of slots, radial protrusions could be formed on stem 24 to interact and bond to adhesive 32.

Figure 6:
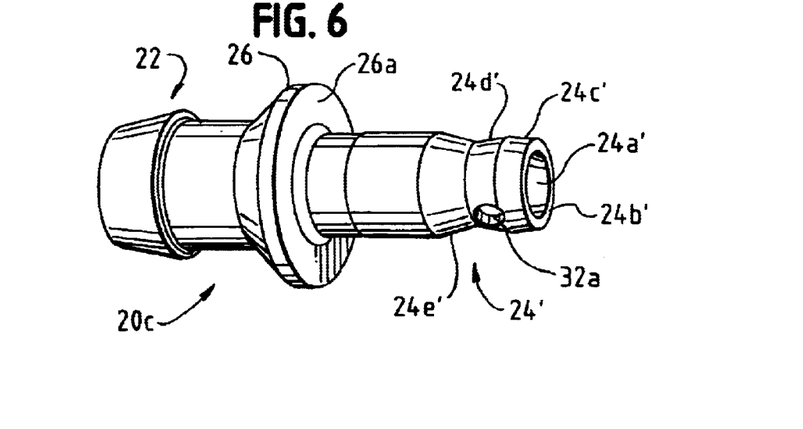
FIG. 6 is a perspective view of an alternate cone in accordance with the present invention.
Figure 7:
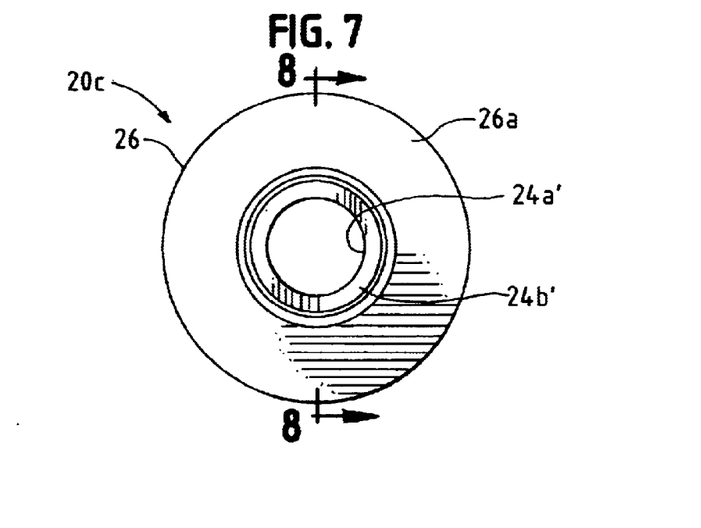
FIG. 7 is an end view of the cone of FIG. 6.
Figure 8:
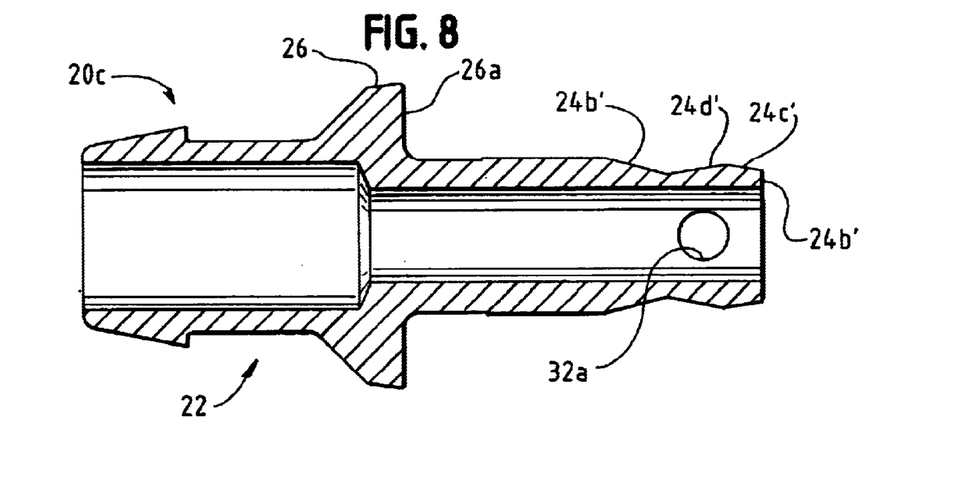
FIG. 8 is a side sectional view of the cone of FIG. 7 taken along plane 8—8 thereof.

FIGS. 6–8 illustrate an alternate form of a cone 20c in accordance with the present invention. Those portions of cone 20c which correspond to the structure of cones 20a, 20b have been assigned to same identification numerals.

In contradistinction to cones 20a, 20b, cone 20c exhibits one or more holes or openings 32a in corresponding stem 24'. It will be understood that as stem 24' is slid into a respective end, such as end 12-1 of insert 12, the adhesive therein flows into opening or openings 32a, 32b as well as into a hollow interior of stem 24' bounded by surface 24a'. This creates a mass of adhesive both within and without stem 24' which when cured and in combination with interior surface 12d of insert 12 resists rotary motion between cone 24' and respective insert 12 and handle 14.

As discussed above, stem 24d' also exhibits first and second reverse tapered surfaces 24d', 24e' which in turn with an interior peripheral surface 12d of the insert 12 form a glue trap precluding axial movement of cone 20c relative to the respective insert/handle combination 12, 14.

It will be understood that while openings 32a have been illustrated as circular, other forms of openings come within the spirit and scope of the present invention.

Figure 9:
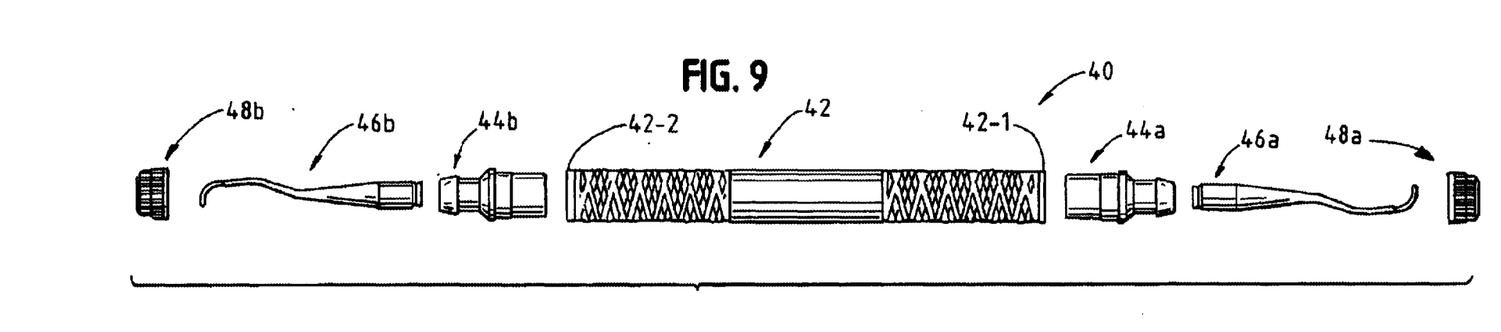
FIG. 9 is an assembly view of an alternate embodiment of the instrument of FIG. 1.

FIG. 9 illustrates an exploded view of an alternate embodiment 40 of an instrument in accordance with the present invention. The instrument 40 includes a cylindrical metal handle 42 which has first and second ends 42-1 and 42-2. In one embodiment, the handle 42 is hollow. Alternately, only the ends 42-1, -2 need be hollow.

Metal cones 44a, 44b are slidably received, for example with a press-fit, within hollow ends 44-1, 44-2 during assembly. Operative instrument tips 46a, 46b are, during assembly, press-fit into respective cones 44a, 44b either before or after the respective cone or cones 44a, 44b is/are inserted into respective ends 42-1, 42-2 of handle 42. Color coded hollow, conical members 48a, 48b are slidably receivable onto respective cones 44a, 44b to provide color coding and additional gripping surfaces for the instrument 40.

Figure 10:
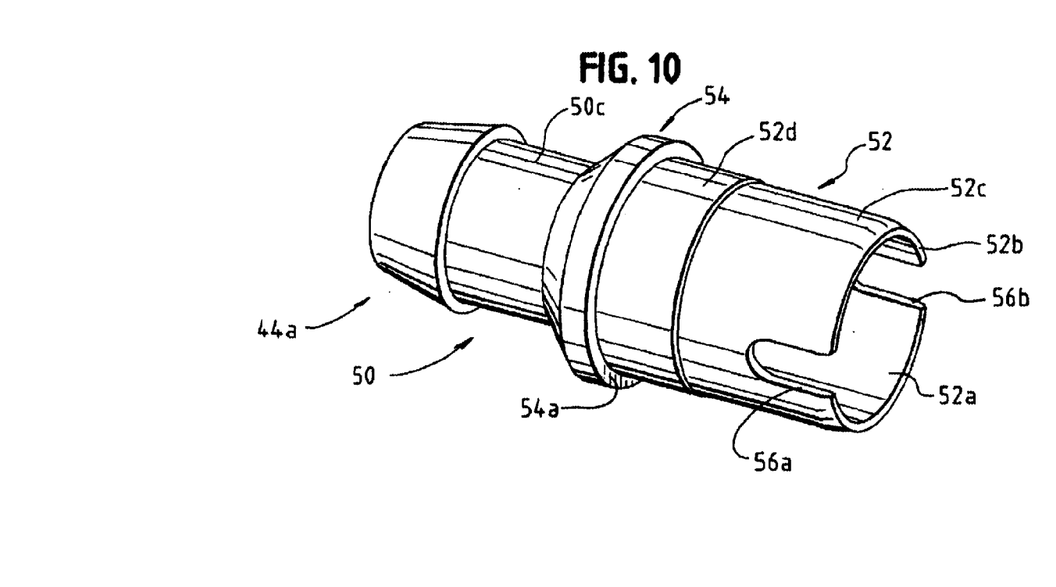
FIG. 10 is a perspective view of an alternate form of a cone usable with the instrument of FIG. 9.
Figure 11:
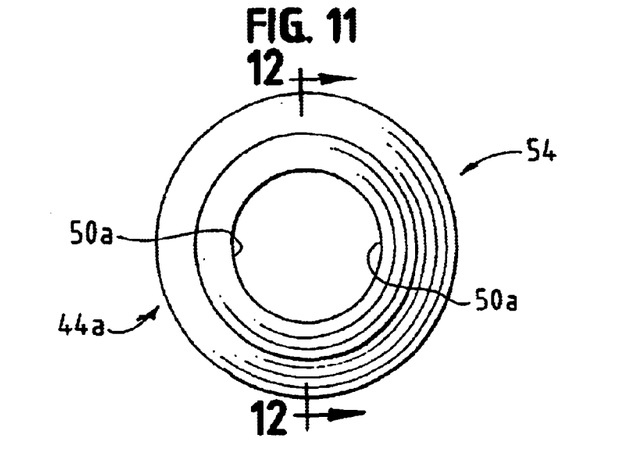
FIG. 11 is an end view of the cone of FIG. 10.
Figure 12:
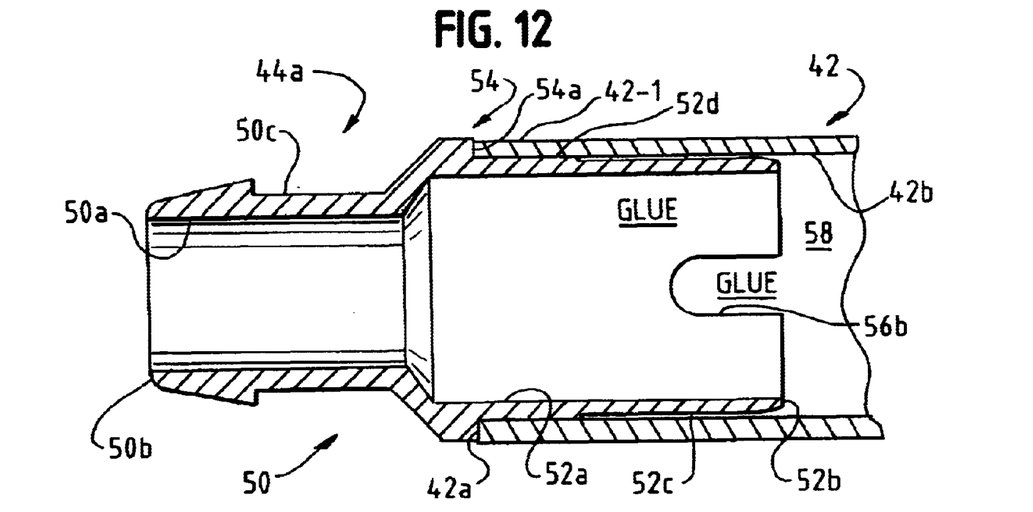
FIG. 12 is a side sectional view of the cone of FIG. 10, taken along plane 12—12 of FIG. 11 in combination with a handle of the instrument of FIG. 9.

The cones 44a, 44b are substantially identical so a description of cone 44a will suffice for both. FIGS. 10, 11 and 12 illustrate various details of the cone 44a alone and in combination with handle 42.

The cone 44a includes a hollow instrument receiving end 50 with an internal cylindrical peripheral surface 50a that terminates in an end 50b. An annular region 50c is provided to receive the respective color coded conical member, such as 48a, 48b. It will be understood that tip 46a, 46b would be press-fit into the hollow tip receiving end 50.

The cone 44a also includes a hollow stem 52 with a cylindrical internal peripheral surface 52a which terminates at an end 52b. The stem 52 includes first and second exterior peripheral surfaces 52c, 52d which abut one another. Surface 52d which has a slightly larger radius than surface 52c terminates at an annular protrusion generally indicated at 54. The protrusion 54 exhibits an annular surface 54a adjacent to exterior cylindrical surface 52d.

The stem 52 also exhibits first and second slots 56a, 56b which terminate at end surface 52b. It will be understood that instead of slots, openings, corresponding to openings 32a, 32b could be formed in the stem 52 without departing from the spirit and scope of the present invention.

During assembly, the hollow end or ends 42-1, 42-2 of handle 42 are filled with glue or adhesive 58. The stem 52, and in particular cylindrical section 52d is then press-fit into end 42-1 of handle 42. In the process, glue 58 flows into and fills slots 56a, 56b, the interior of hollow stem 52 and the spaces between interior peripheral surface 42b and exterior peripheral surface 52c.

When the glue 58 has been cured, it provides a solid mass which in combination with stem 52 and end 42-1 resists rotation of the cone 44a relative to the metal handle 42.

While the instrument 40 has been illustrated and explained in terms of a double-ended instrument, it will be understood that single ended instruments come within the spirit and scope of the present invention.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A dental instrument comprising:
    an elongated metal tube, hollow at least at one end, having an exterior periphery and first and second spirals formed in the periphery;
    an overmolded plastic handle locked axially and rotatably to the metal tube;
    at least one cone having a stem and an instrument receiving portion wherein the stem includes at least one glue receiving feature whereby when the stem is inserted into a glue filled hollow end of the tube, the glue interacts with the feature and when cured, locks the cone to the tube to prevent at least rotation of the cone relative to the tube.

2. An instrument as in claim 1 wherein the glue feature comprises one of a slot in the stem, a hole in the stem, and a protrusion from the stem.

3. An instrument as in claim 2 which carries at least one treatment tip wherein the tip engages the instrument receiving portion of the cone with an interference fit.

4. An instrument as in claim 3 wherein the glue receiving feature comprises an axially oriented elongated slot formed in the stem wherein the instrument resists an applied torque in excess of 35 inch-pounds without rotation of the cone relative to the handle.

5. An instrument as in claim 1 wherein the stem is hollow, cylindrical and extends axially from the cone exhibiting a free end.

6. An instrument as in claim 5 wherein the glue receiving feature comprises one of a slot formed in the free end, a hole formed in the free end and, at least one glue contacting protrusion formed on the free end.

7. An instrument as in claim 1 wherein the glue receiving feature includes a region which interacts with cured glue to preclude axial movement of the cone relative to the tube.

8. An instrument as in claim 1 wherein the glue receiving feature includes a first external tapered region on the stem.

9. An instrument as in claim 8 wherein the glue receiving feature includes a second, external tapered region on the stem.

10. An instrument as in claim 9 wherein the first and second tapered regions are opposed to one another and intersect along a common circumference thereby providing a laterally located, symmetrical glue receiving region which when cured prevents axial movement of the cone relative to the tube.

11. A dental treatment structure comprising:
    a hollow stem having first and second ends wherein a lateral glue receiving opening is formed adjacent to one of the ends;
    an instrument receiving segment, coupled to the other end, on a common centerline, wherein the segment defines a symmetrical opening for receipt of a dental treatment applicator.

12. A structure as in claim 11 wherein the instrument receiving segment comprises a conical cross section which tapers toward the opening.

13. A dental treatment structure comprising:
    a hollow stem having first and second ends wherein a lateral glue receiving opening is formed adjacent to one of the ends;
    an instrument receiving segment, coupled to the other end, on a common centerline, wherein the segment defines a symmetrical opening for receipt of a dental treatment applicator which includes one of an elongated metal handle with a stem receiving opening in at least one end thereof, and, a plastic handle with an elongated, centrally located stem receiving opening in at least one end thereof whereby glue in the opening of the selected handle fills the glue receiving opening, and when cured, forms a laterally extending obstruction which couples rotary motion between the selected handle and stem precluding relative motion therebetween.

14. A structure as in claim 13 wherein the plastic handle includes a hollow, axially oriented metal reinforcement.

15. A structure as in claim 14 wherein the metal reinforcement has an external periphery and carries at least one spiral thereon.

16. A structure as in claim 15 wherein the reinforcement carries at least first and second reverse spirals.

17. A structure as in claim 14 wherein the plastic handle carries molded gripping features on an exterior periphery thereof.

18. A method of assembling a dental instrument comprising:

forming an elongated handle with at least one hollow end;
   placing glue in the follow end;
   inserting a stem of an instrument supporting apparatus into the hollow end causing the glue to flow thereinto;
   curing the glue thereby forming a hardened glue mass which extends one of, in part radially through an opening in the stem, and, in part radially relative to a protrusion from the stem.

19. A method as in claim 18 which includes subjecting the handle and the apparatus to a torque of at least 35 inch-pounds; and rejecting those which do not pass the test.

20. A method as in claim 18 wherein the forming step includes:

providing an elongated metal insert;
   molding a resin handle around the insert; and
   curing the resin handle.

21. A method as in claim 20 which includes molding the resin handle so that an end portion of the resin extends axially past an end surface of metal insert.

22. A method as in claim 21 which includes attaching the apparatus to the end of the metal insert with an the end of the resin handle abutting a surface of the instrument supporting apparatus.

23. A method as in claim 22 which includes forming at least one spiral on an exterior peripheral surface of the metal insert.

24. A method as in claim 23 which includes forming dual, reverse spirals on the exterior peripheral surface.

25. A method as in claim 18 wherein the forming step includes forming an elongated metal handle.

26. A method as in claim 18 which includes attaching a treatment applying tip to the instrument supporting apparatus.

27. A dental treatment structure comprising:

a hollow stem having first and second ends where a lateral glue receiving opening is formed adjacent to one of the ends;

an instrument receiving segment, coupled to the other end, on a common centerline, where the segment has an external periphery, displaced from the glue receiving opening, with a varying radius and there the segment defines a symmetrical opening for receipt of a dental treatment applicator.

28. A structure as in claim 27 wherein the instrument receiving segment comprises a conical cross section which tapers toward the opening.

29. A structure as in claim 27 which includes one of an elongated metal handle with a stem receiving opening in at least one end thereof, or, a plastic handle with an elongated, centrally located stem receiving opening in at least one end thereof whereby glue in the opening of the selected handle fills the glue receiving opening, and when cured, forms a laterally extending obstruction which couples rotary motion between the selected handle and stem precluding relative motion therebetween.

* * * * *